(12) United States Patent
Tankiewicz et al.

(10) Patent No.: US 9,867,540 B2
(45) Date of Patent: Jan. 16, 2018

(54) CO-PLANAR, NEAR FIELD COMMUNICATION TELEMETRY LINK FOR AN ANALYTE SENSOR

(71) Applicant: Senseonics, Incorporated, Germantown, MD (US)

(72) Inventors: Szymon Tankiewicz, Germantown, MD (US); Joshua C. Schaefer, Germantown, MD (US); Andrew DeHennis, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 584 days.

(21) Appl. No.: 14/453,230

(22) Filed: Aug. 6, 2014

(65) Prior Publication Data

US 2015/0045635 A1  Feb. 12, 2015

Related U.S. Application Data

(60) Provisional application No. 61/864,174, filed on Aug. 9, 2013.

(51) Int. Cl.
| | | |
|---|---|---|
| *A61B 5/145* | (2006.01) | |
| *A61B 5/00* | (2006.01) | |
| *A61B 5/1455* | (2006.01) | |
| *A61B 5/1459* | (2006.01) | |

(52) U.S. Cl.
CPC ............ *A61B 5/0031* (2013.01); *A61B 5/002* (2013.01); *A61B 5/0004* (2013.01); *A61B 5/14503* (2013.01); *A61B 5/1459* (2013.01); *A61B 5/14532* (2013.01); *A61B 5/14556* (2013.01)

(58) Field of Classification Search
CPC . A61B 5/0031; A61B 5/14503; A61B 5/0004; A61B 5/002
See application file for complete search history.

(56) References Cited

U.S. PATENT DOCUMENTS

| | | |
|---|---|---|
| 5,512,246 A | 4/1996 | Russell et al. |
| 5,517,313 A | 5/1996 | Colvin, Jr. |
| 8,634,928 B1 * | 1/2014 | O'Driscoll ........... A61N 1/3787 607/33 |
| 2007/0145830 A1 | 6/2007 | Lee et al. |

(Continued)

FOREIGN PATENT DOCUMENTS

WO  2013/055962 A1  4/2013

*Primary Examiner* — Eric Winakur
(74) *Attorney, Agent, or Firm* — Rothwell, Figg, Ernst & Manbeck, P.C.

(57) ABSTRACT

An inductive sensor system for remote powering and communication with an analyte sensor (e.g., a fully implantable analyte sensor). The system may include an analyte sensor and transceiver. The system may be ferrite-enhanced. The transceiver may implement a passive telemetry for communicating with the analyte sensor via an inductive magnetic link for both power and data transfer. The link may be a co-planar, near field communication telemetry link. The transceiver may include a reflection plate configured to focus flux lines linking the transceiver and the sensor uniformly beneath the transceiver. The transceiver may include an amplifier configured to amplify battery power and provide radio frequency (RF) power to a transceiver antenna.

15 Claims, 14 Drawing Sheets

(56) References Cited

U.S. PATENT DOCUMENTS

| | | |
|---|---|---|
| 2009/0227882 A1 | 9/2009 | Foo |
| 2009/0234407 A1 | 9/2009 | Hastings et al. |
| 2011/0152971 A1 | 6/2011 | Nghiem et al. |
| 2012/0206097 A1* | 8/2012 | Soar ..................... H02J 5/005 320/108 |
| 2013/0113669 A1 | 5/2013 | Bellows |

* cited by examiner

CO-PLANAR, NEAR FIELD COMMUNICATION TELEMETRY LINK FOR AN ANALYTE SENSOR

CROSS-REFERENCE TO RELATED APPLICATION

The present application claims the benefit of priority to U.S. Provisional Application Ser. No. 61/864,174, filed on Aug. 9, 2013, which is incorporated by reference in its entirety.

BACKGROUND

Field of Invention

The present invention relates generally to measuring an analyte in a medium of a living animal using a system including a transceiver and a sensor. Specifically, the present invention relates to a co-planar, near field communication telemetry link between the transceiver and the sensor capable of transcutaneous communication.

Discussion of the Background

A sensor may be implanted within a living animal (e.g., a human) used to measure an analyte (e.g., glucose or oxygen) in a medium (e.g., interstitial fluid (ISF), blood, or intraperitoneal fluid) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure an analyte are described in U.S. Pat. Nos. 5,517,313 and 5,512,246, which are incorporated herein by reference in their entireties.

There is presently a need in the art for an improved inductive magnetic link for both powering and communicating with an analyte sensor.

SUMMARY

The present invention overcomes the disadvantages of prior systems by providing, among other advantages, an improved inductive magnetic link for both powering and communicating with an analyte sensor.

One aspect of the invention may provide a sensor system for detecting an amount or concentration of an analyte in vivo within a living organism. The sensor system may include an analyte sensor and a transceiver. The analyte sensor may include a sensor antenna. The transceiver may be configured to interface with the analyte sensor, and the transceiver may include a transceiver antenna configured to convey a power signal to the analyte sensor and to receive data signals from the analyte sensor. The transceiver antenna and sensor antenna may be configured to provide a co-planar, near field communication telemetry link between the transceiver and the sensor capable of transcutaneous communication. In some embodiments, the transceiver antenna and sensor antenna may be capable of transcutaneous communication across a distance greater than or equal to 0.5 inches.

Another aspect of the invention may provide a transceiver for interfacing with an analyte sensor. The transceiver may include an interface device and a reflection plate. The interface device may be configured to convey a power signal to the analyte sensor and to receive data signals from the analyte sensor. In some embodiments, the reflection plate may be configured to focus flux lines linking the interface device and the analyte sensor uniformly beneath the transceiver.

Still another aspect of the invention may provide a transceiver for interfacing with an analyte sensor. The transceiver may include an antenna, a battery, and an amplifier. The antenna may be configured to convey a power signal to the analyte sensor and to receive data signals from the analyte sensor. The battery may be configured to provide battery power. The amplifier may be configured to amplify the battery power and provide radio frequency (RF) power to the antenna. The provided RF power may be sufficient to power the analyte sensor at a required range.

Yet another aspect of the invention is a transceiver for interfacing with an analyte sensor. The transceiver may include an antenna, an antenna fault detection circuit, and a microcontroller. The antenna may be configured to convey a power signal to the analyte sensor and to receive data signals from the analyte sensor. The antenna fault detection circuit configured to output a voltage proportional to a field strength of the antenna. The microcontroller configured to measure the voltage output by the antenna fault detection circuit and determine whether the antenna is emitting a strong enough signal.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
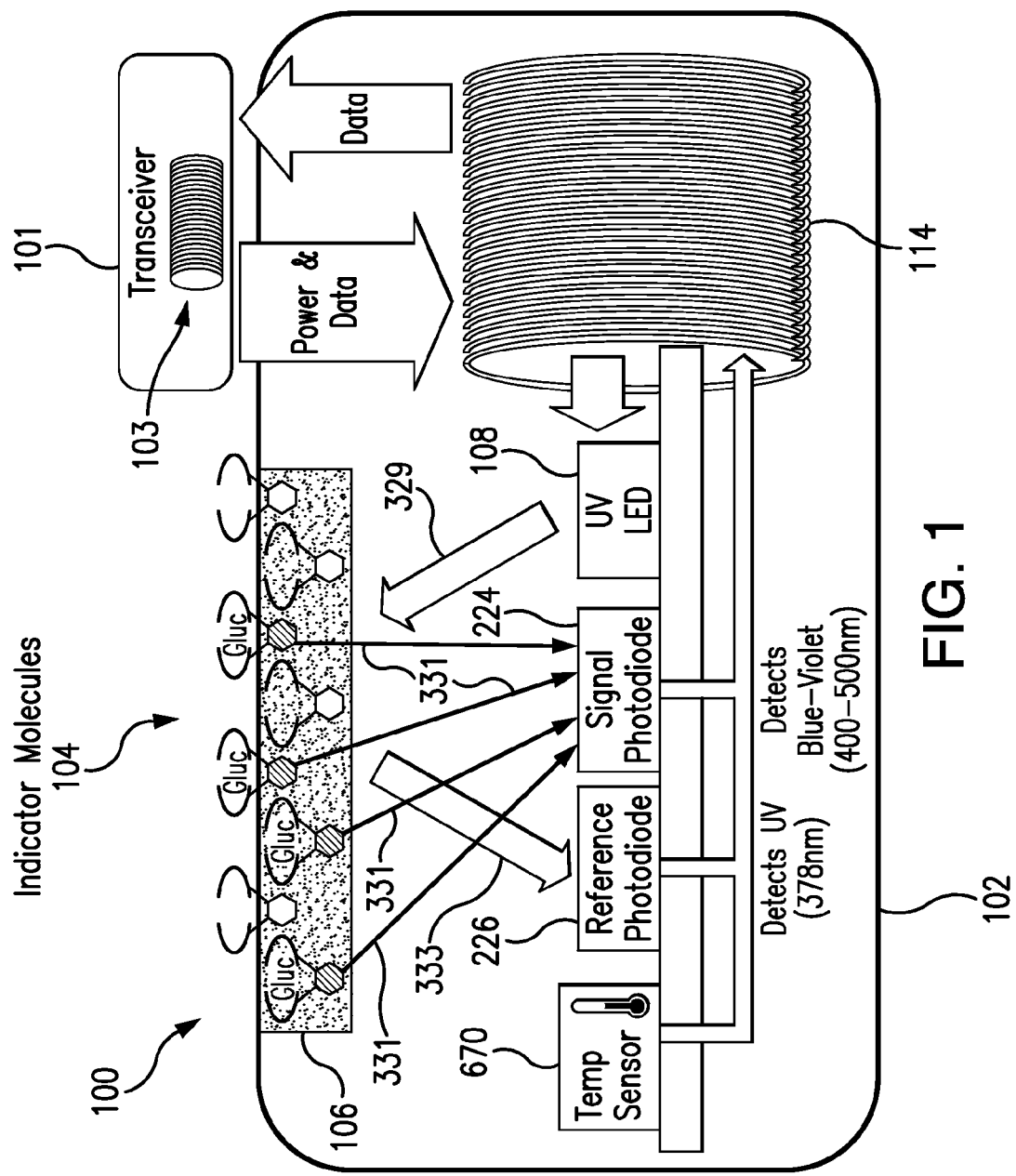
FIG. 1 is a schematic view illustrating a sensor system embodying aspects of the present invention.

FIG. 1 is a schematic view of a sensor system embodying aspects of the present invention. In one non-limiting embodiment, the system includes a sensor 100 and an external transceiver 101. In the embodiment shown in FIG. 1, the sensor 100 may be capable of implantation in a living animal (e.g., a living human). The sensor 100 may be implanted, for example, in a living animal's arm, wrist, leg, abdomen, peritoneum, or other region of the living animal suitable for sensor implantation. For example, in one non-limiting embodiment, the sensor 100 may be implanted beneath the skin (i.e., in the subcutaneous or peritoneal tissues). In some embodiments, the sensor 100 may be an optical sensor (e.g., a fluorometer). In some embodiments, the sensor 100 may be a chemical or biochemical sensor.

A transceiver 101 may be an electronic device that communicates with the sensor 100 to power the sensor 100 and/or receive measurement information (e.g., photodetector and/or temperature sensor readings) from the sensor 100. The measurement information may include one or more readings from one or more photodetectors of the sensor and/or one or more readings from one or more temperature sensors of the sensors. In some embodiments, the transceiver 101 may calculate analyte (e.g., glucose or oxygen) concentrations from the measurement information received from the sensor 100.

In some embodiments, the sensor system may provide real-time readings, graphs, trends, and/or analyte alarms directly to a user. The system may be capable of being used in a home setting, and, in embodiments where the analyte is glucose, the system may aid people with diabetes in predicting and detecting episodes of hypoglycemia and hyperglycemia. The system may additionally or alternatively be capable of being used in clinical settings to aid health care professionals in evaluating analyte control. In contrast to analyte monitoring systems currently available on the market, the transceiver 101 implements a passive telemetry for communicating with the analyte sensor 100 via an inductive magnetic link for both power and data transfer. The sensor 100 may include an inductive element 114, which may be, for example, a ferrite based micro-antenna. In some embodiments, the inductive element may be connected to microfluorimeter circuitry (e.g., an application specification integrated circuit (ASIC)) and a related optical detection system of the sensor 100. The sensor 100 may not include a battery, and, as a result, the sensor 100 may rely on the transceiver 101 to provide necessary power and a data link to convey analyte-related data back to transceiver 101.

In one non-limiting embodiment, the sensor system may continually record interstitial fluid glucose levels in people with diabetes mellitus for the purpose of improving diabetes management. The transceiver 101 may be wearable and may communicate with the sensor 100, which may be a passive, fully implantable sensor. In a non-limiting embodiment, the analyte sensor 100 may have the approximate size of a grain of rice. The transceiver 101 may provide energy to run the sensor 100, which may or may not have an internal power source (e.g., a battery), via a magnetic field. In some embodiments, the magnetic transceiver-sensor link can be considered as "weakly coupled transformer" type. The magnetic transceiver-sensor link may provide energy and a link for date transfer using, for example, amplitude modulation (AM). Although in some embodiments, data transfer is carried out using AM, in alternative embodiments, other types of modulation may be used. The magnetic transceiver-sensor link may have a low efficiency of power transfer and, therefore, may require relatively high power amplifier to energize the sensor 100 at longer distances. In some non-limiting embodiments, the sensor system may use a frequency of 13.56 MHz, which can achieve high penetration through the skin and is a medically approved frequency band, for power transfer.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive (e.g., as part of a biocompatible patch), and the transceiver 101 may convey (e.g., periodically, such as every two minutes, and/or upon user initiation) measurement commands (i.e., requests for measurement information) to the sensor 100. In some embodiments where the transceiver 101 is a handheld device (e.g., a smartphone, a tablet, a medical application-specific handheld device, or other handheld computing device), positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a reading from the sensor 100.

In some embodiments, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive data (e.g., measurement information) from the sensor 100. For example, in a non-limiting embodiment, the transceiver 101 may receive data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some embodiments, the sensor 100 includes a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)).

In some embodiments, sensor 100 may include an analyte indicator. In some non-limiting embodiments, the analyte indicator may be a polymer graft 106 coated, diffused, adhered, or embedded on at least a portion of the exterior surface of the sensor housing 102. The polymer graft 106 may cover the entire surface of sensor housing 102 or only one or more portions of the surface of housing 102. As an alternative to coating the graft 106 on the outer surface of sensor housing 102, the graft 106 may be disposed on the outer surface of the sensor housing 102 in other ways, such as by deposition or adhesion. In some embodiments, the polymer graft 106 may be a fluorescent glucose indicating polymer. In one non-limiting embodiment, the polymer is biocompatible and stable, grafted onto the surface of sensor housing 102, designed to allow for the direct measurement of glucose in interstitial fluid (ISF), blood, or intraperitoneal fluid after implantation of the sensor 100.

In some embodiments, the analyte indicator (e.g., polymer graft 106) of the sensor 100 may include indicator molecules 104. The indicator molecules 104 may be distributed throughout the entire graft 106 or only throughout one or more portions of the graft 106. The indicator molecules 104 may be, for example, fluorescent indicator molecules or absorption indicator molecules. In some embodiments, the indicator molecules 104 may reversibly bind an analyte (e.g., glucose or oxygen). When an indicator molecule 104 has bound an analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 to 500 nm. When no analyte is bound, the indicator molecule 104 may be only weakly fluorescent.

In some embodiments, the sensor 100 may include a light source 108, which may be, for example, a light emitting diode (LED) or other light source that emits radiation, including radiation over a range of wavelengths that interact with the indicator molecules 104. In other words, the light source 108 may emit the excitation light 329 that is absorbed by the indicator molecules in the matrix layer/polymer 104. As noted above, in one non-limiting embodiment, the light source 108 may emit excitation light 329 at a wavelength of approximately 378 nm.

In some embodiments, the sensor 100 may also include one or more photodetectors (e.g., photodiodes, phototransistors, photoresistors or other photosensitive elements). For example, in the embodiment illustrated in FIG. 1, sensor 100 has a first photodetector 224 and a second photodetector 226. However, this is not required, and, in some alternative embodiments, the sensor 100 may only include the first photodetector 224. In the case of a fluorescence-based sensor, the one or more photodetectors may be sensitive to fluorescent light emitted by the indicator molecules 104 such that a signal is generated by a photodetector (e.g., photodetector 224) in response thereto that is indicative of the level of fluorescence of the indicator molecules and, thus, the amount of analyte of interest (e.g., glucose).

Some part of the excitation light 329 emitted by the light source 108 may be reflected from the polymer graft 106 back into the sensor 100 as reflection light 331, and some part of the absorbed excitation light may be emitted as emitted (fluoresced) light 331. In one non-limiting embodiment, the emitted light 331 may have a different wavelength than the wavelength of the excitation light 329. The reflected light 333 and emitted (fluoresced) light 331 may be absorbed by the one or more photodetectors (e.g., first and second photodetectors 224 and 226) within the body of the sensor 100.

Each of the one or more photodetectors may be covered by a filter 112 (see FIG. 3) that allows only a certain subset of wavelengths of light to pass through. In some embodiments, the one or more filters 112 may be thin glass filters. In some embodiments, the one or more filters 112 may be thin film (e.g., dichroic) filters deposited on the glass and may pass only a narrow band of wavelengths and otherwise reflect most of the received light. In some embodiments, the filters may be thin film (dichroic) filters deposited directly onto the photo detectors and may pass only a narrow band of wavelengths and otherwise reflect most of the light received thereby. The filters 112 may be identical (e.g., both filters 112 may allow signals to pass) or different (e.g., one filter 112 may be a reference filter and another filter 112 may be a signal filter).

In one non-limiting embodiment, the second (reference) photodetector 226 may be covered by a reference photodiode filter that passes light at the same wavelength as is emitted from the light source 108 (e.g., 378 nm). The first (signal) photodetector 224 may detect the amount of fluoresced light 331 that is emitted from the molecules 104 in the graft 106. In one non-limiting embodiment, the peak emission of the indicator molecules 104 may occur around 435 nm, and the first photodetector 224 may be covered by a signal filter that passes light in the range of about 400 nm to 500 nm. In some embodiments, higher glucose levels/concentrations correspond to a greater amount of fluorescence of the molecules 104 in the graft 106, and, therefore, a greater number of photons striking the first photodetector 224.

In some embodiments, sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components. In some embodiments, circuitry of the sensor 100 may incorporate some or all of the structure described in U.S. patent application Ser. No. 13/650,016, which is incorporated herein by reference in its entirety, with particular reference to FIG. 11D.

In some embodiments, the one or more photodetectors (e.g., photodetectors 224 and 226) may be mounted on the semiconductor substrate 116, but, in some preferred embodiments, the one or more photodetectors may be fabricated in the semiconductor substrate 116. In some embodiments, the light source 108 may be mounted on the semiconductor substrate 116. For example, in a non-limiting embodiment, the light source 108 may be flip-chip mounted on the semiconductor substrate 116. However, in some embodiments, the light source 108 may be fabricated in the semiconductor substrate 116.

Figure 2:
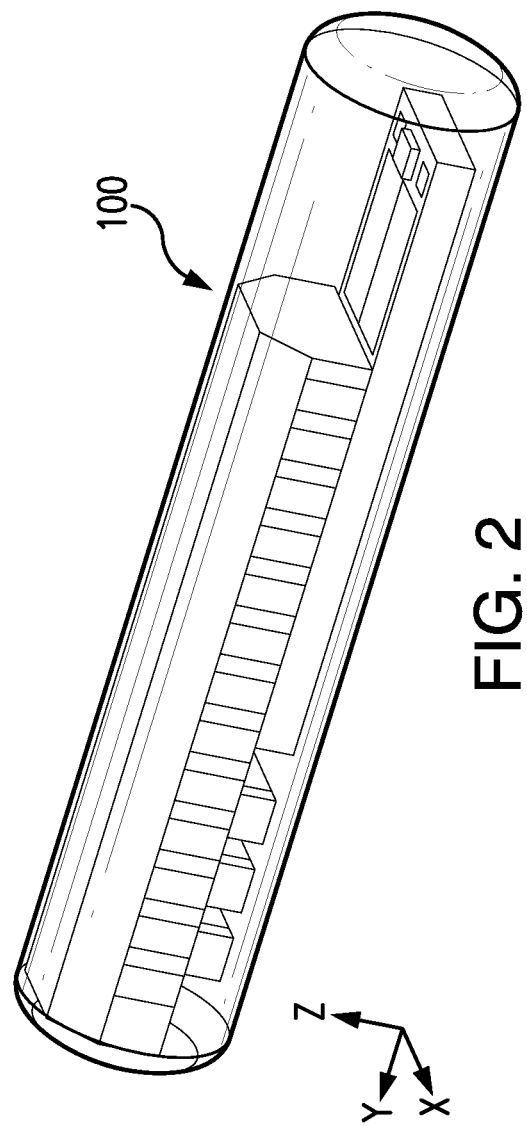
FIG. 2 illustrates a perspective view of a sensor embodying aspects of the present invention.
Figure 3:
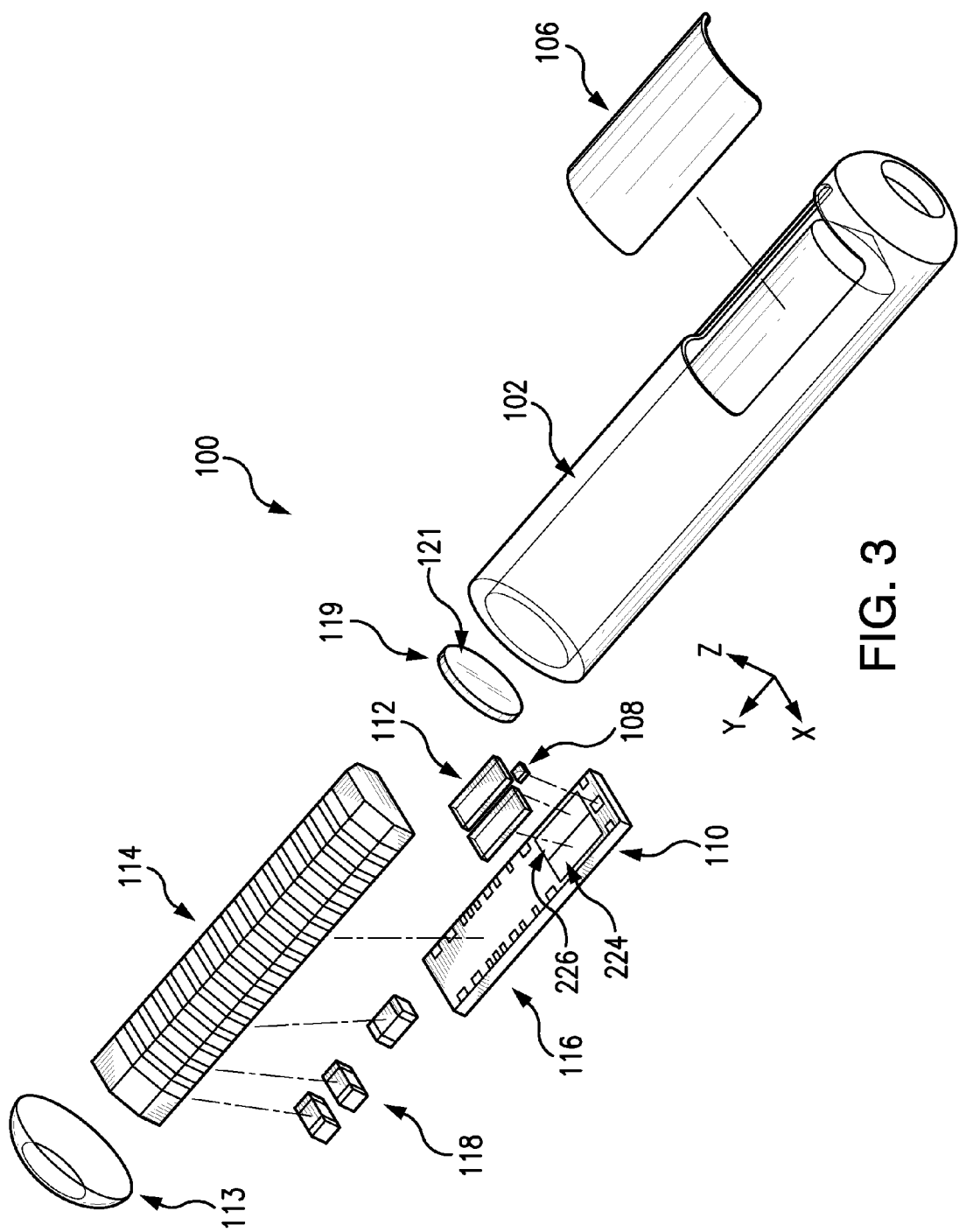
FIG. 3 illustrates an exploded view of a sensor embodying aspects of the present invention.

FIGS. 2-7 illustrate a non-limiting embodiment of a sensor 100 embodying aspects of the present invention that may be used in the sensor system illustrated in FIG. 1. FIGS. 2 and 3 illustrate perspective and exploded views, respectively, of the non-limiting embodiment of the sensor 100.

In some embodiments, as illustrated in FIG. 3, the sensor 100 may include one or more capacitors 118. The one or more capacitors 118 may be, for example, one or more tuning capacitors and/or one or more regulation capacitors. Further, the one or more capacitors 118 may be in addition to one or more capacitors fabricated in the semiconductor substrate 116.

In some embodiments, as illustrated in FIG. 3, the sensor 100 may include a reflector 119 (i.e., mirror). Reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from entering the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen, toxins, pharmaceuticals or other drugs, hormones, and other metabolic analytes in, for example, the human body.

The specific composition of the polymer graft 106 and the indicator molecules 104 may vary depending on the particular analyte the sensor is to be used to detect and/or where the sensor is to be used to detect the analyte (e.g., in the in subcutaneous tissues, blood, or peritoneum). Preferably, however, graft 106 should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

Figure 4:
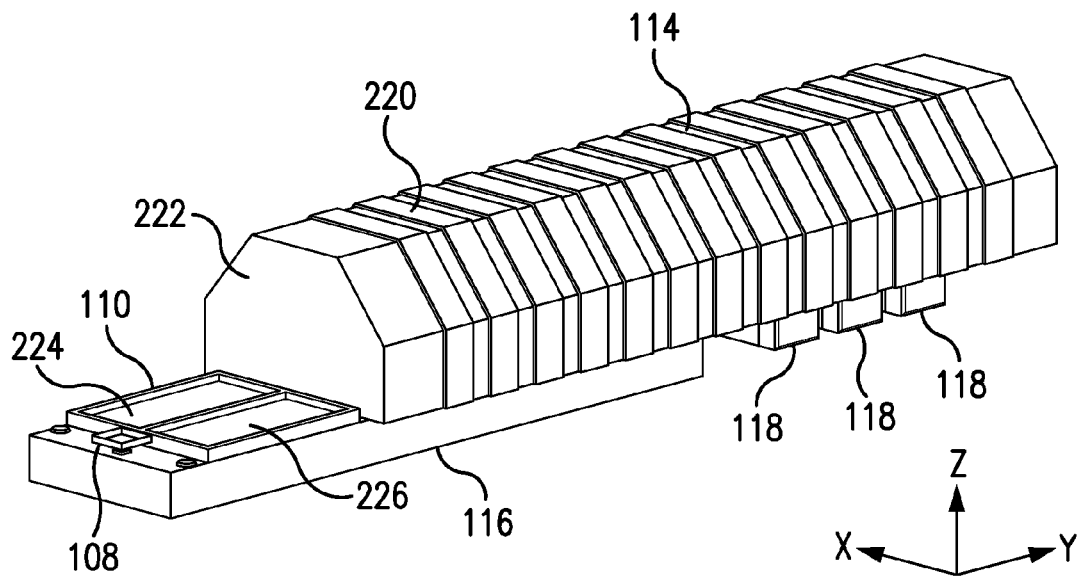
FIGS. 4 and 5 illustrate perspective views of sensor components within the sensor body/shell/capsule of a sensor embodying aspects of the present invention.
Figure 5:
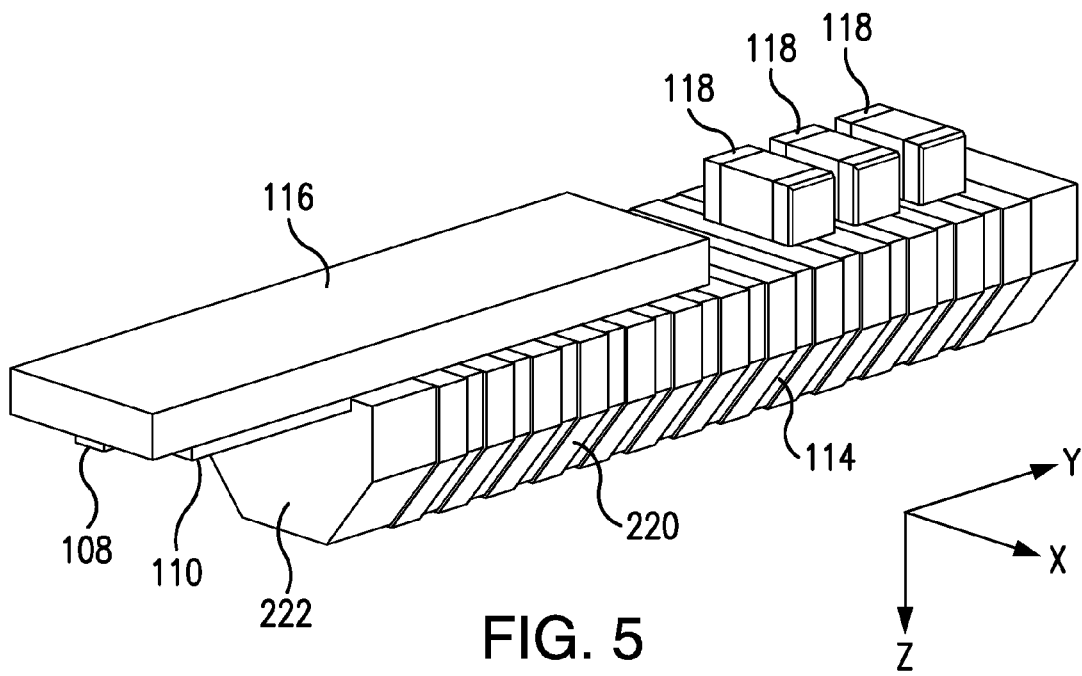

FIGS. 4 and 5 illustrate perspective views of the sensor 100. In FIGS. 4 and 5, the sensor housing 102, filters 112, and the reflector 119, which may be included in some embodiments of the sensor 100, are not illustrated. As shown in the illustrated embodiment, the inductive element 114 may comprise a coil 220. In one embodiment, coil 220 may be a copper coil but other conductive materials, such as, for example, screen printed gold, may alternatively be used. In some embodiments, the coil 220 is formed around a ferrite core 222. Although core 222 is ferrite in some embodiments, in other embodiments, other core materials may alternatively be used. In some embodiments, coil 220 is not formed around a core. Although coil 220 is illustrated as a cylindrical coil in FIGS. 4 and 5, in other embodiments, coil 220 may be a different type of coil, such as, for example, a flat coil.

In some embodiments, coil 220 is formed on ferrite core 222 by printing the coil 220 around the ferrite core 222 such that the major axis of the coil 220 (magnetically) is parallel to the longitudinal axis of the ferrite core 222. A non-limiting example of a coil printed on a ferrite core is described in U.S. Pat. No. 7,800,078, which is incorporated herein by reference in its entirety. In an alternative embodiment, coil 220 may be a wire-wound coil. However, embodiments in which coil 220 is a printed coil as opposed to a wire-wound coil are preferred because each wire-wound coil is slightly different in characteristics due to manufacturing tolerances, and it may be necessary to individually tune each sensor that uses a wire-wound coil to properly match the frequency of operation with the associated antenna. Printed coils, by contrast, may be manufactured using automated techniques that provide a high degree of reproducibility and homogeneity in physical characteristics, as well as reliability, which is important for implant applications, and increases cost-effectiveness in manufacturing.

In some embodiments, a dielectric layer may be printed on top of the coil 220. The dielectric layer may be, in a non-limiting embodiment, a glass based insulator that is screen printed and fired onto the coil 220. In an exemplary embodiment, the one or more capacitors 118 and the semiconductor substrate 116 may be mounted on vias through the dielectric.

In the illustrated embodiment, the one or more photodetectors 110 include a first photodetector 224 and a second photodetector 226. First and second photodetectors 224 and 226 may be mounted on or fabricated in the semiconductor substrate 116.

Figure 6:
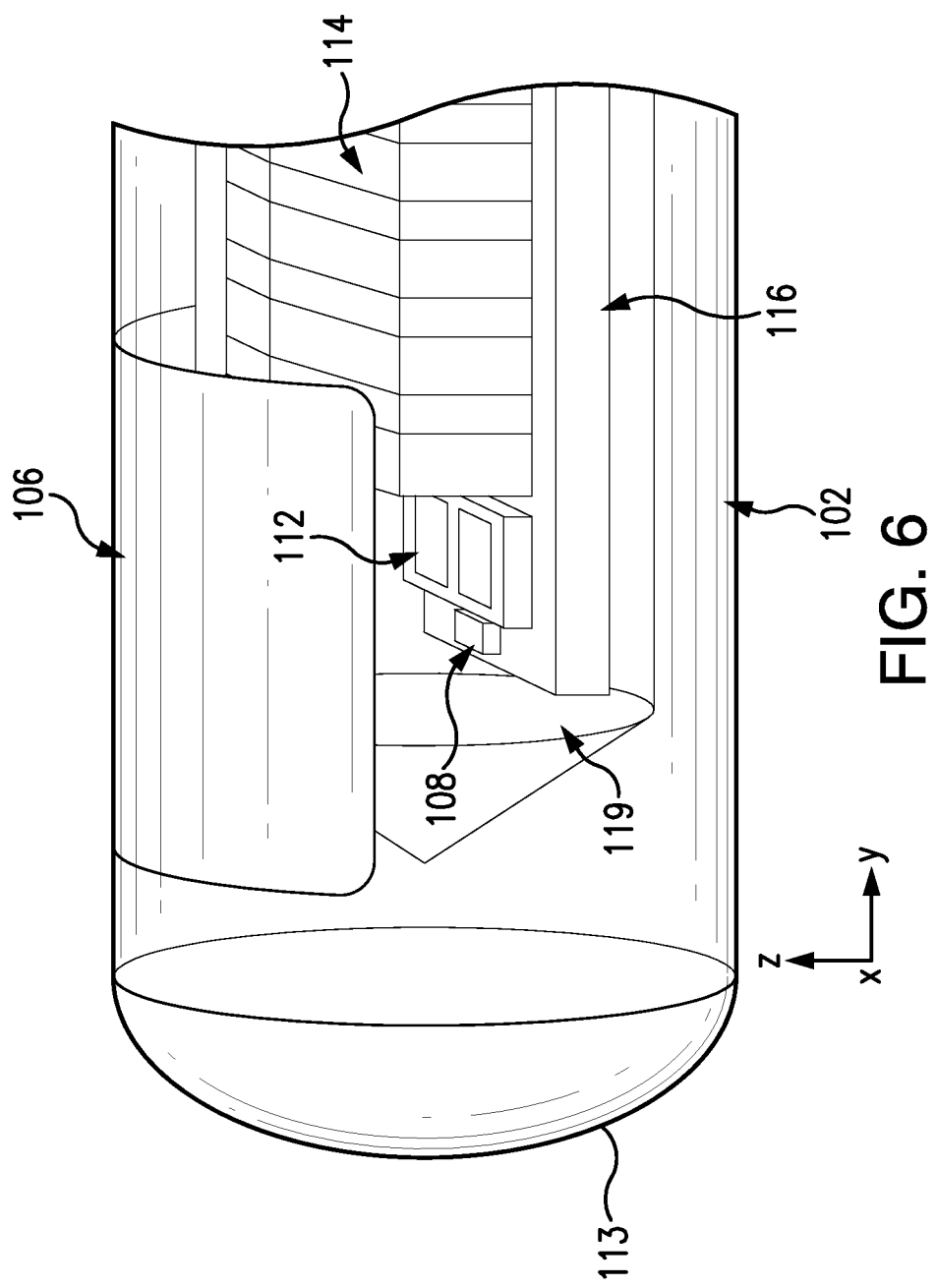
FIG. 6 illustrates a side view of a sensor embodying aspects of the present invention.
Figure 7:
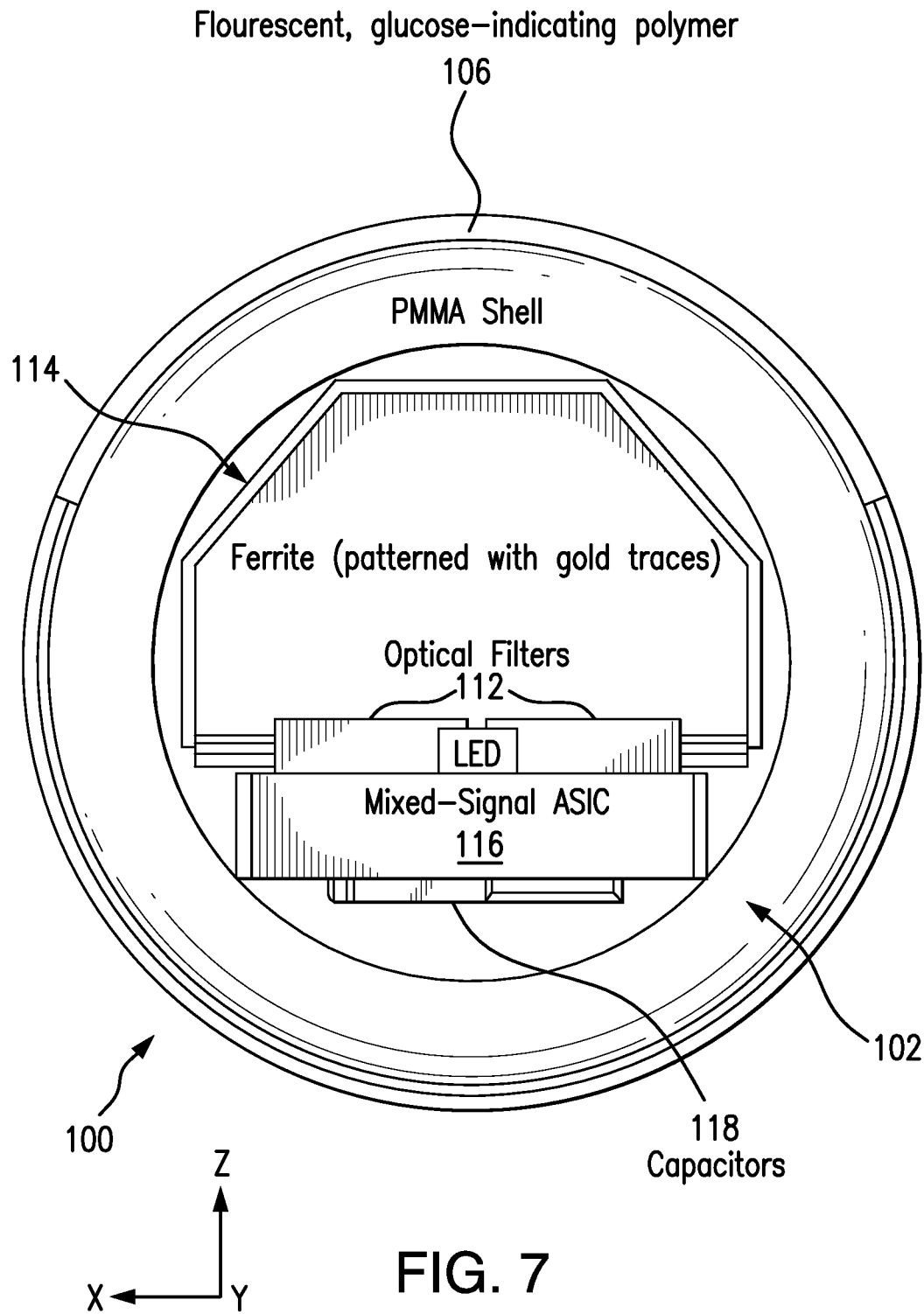
FIG. 7 illustrates a cross-sectional end view of a sensor embodying aspects of the present invention.

FIGS. 6 and 7 illustrate side and cross-sectional views, respectively, of the sensor 100 according to one embodiment. As illustrated in FIGS. 6 and 7, the light source 108 may be positioned to emit light that travels within the sensor housing 102 and reaches the indicator molecules 104 of the polymer graft 106, and the photodetectors 110, which may be located beneath filters 112, may be positioned to receive light from the indicator molecules 104 of the polymer graft 106.

Figure 8:
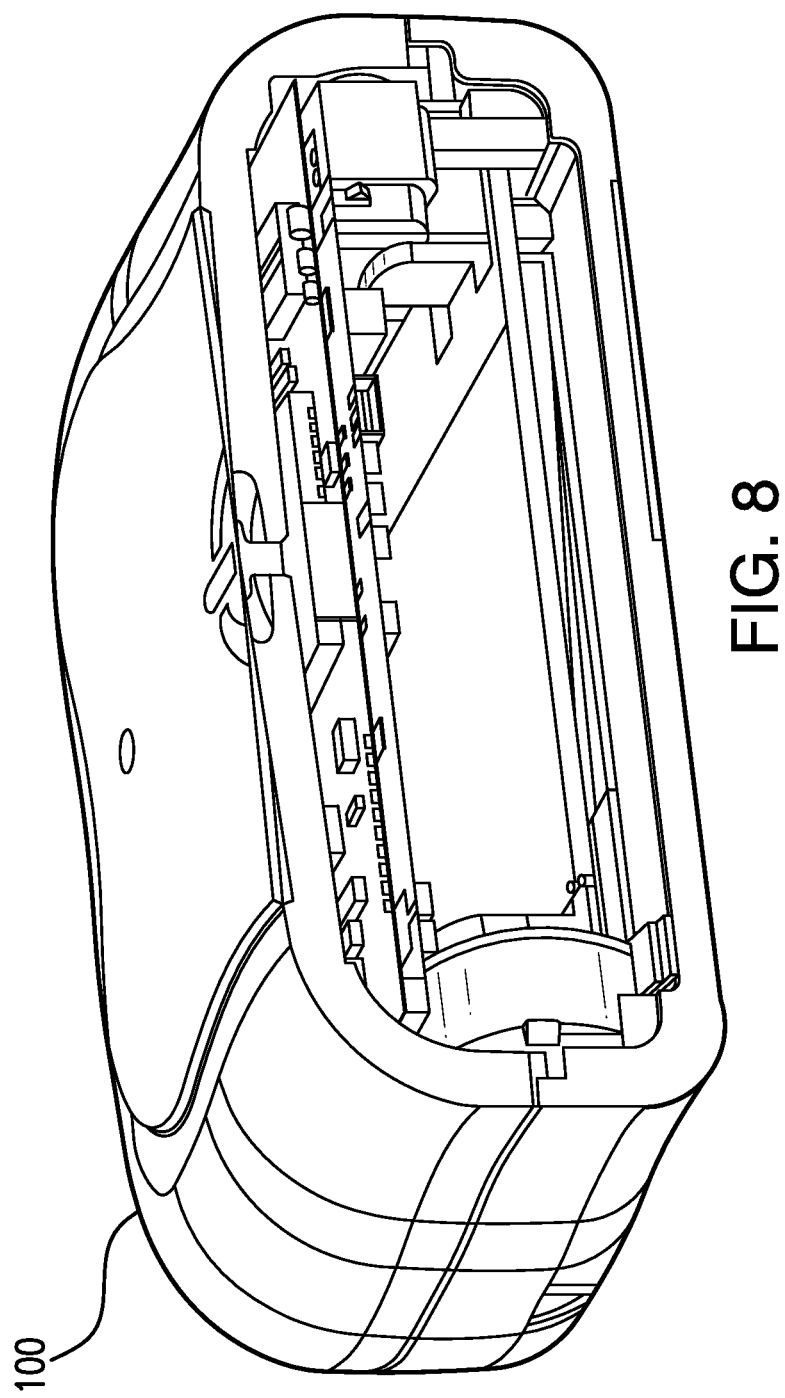
FIG. 8 is cross-sectional, perspective view of a transceiver embodying aspects of the invention.
Figure 9:
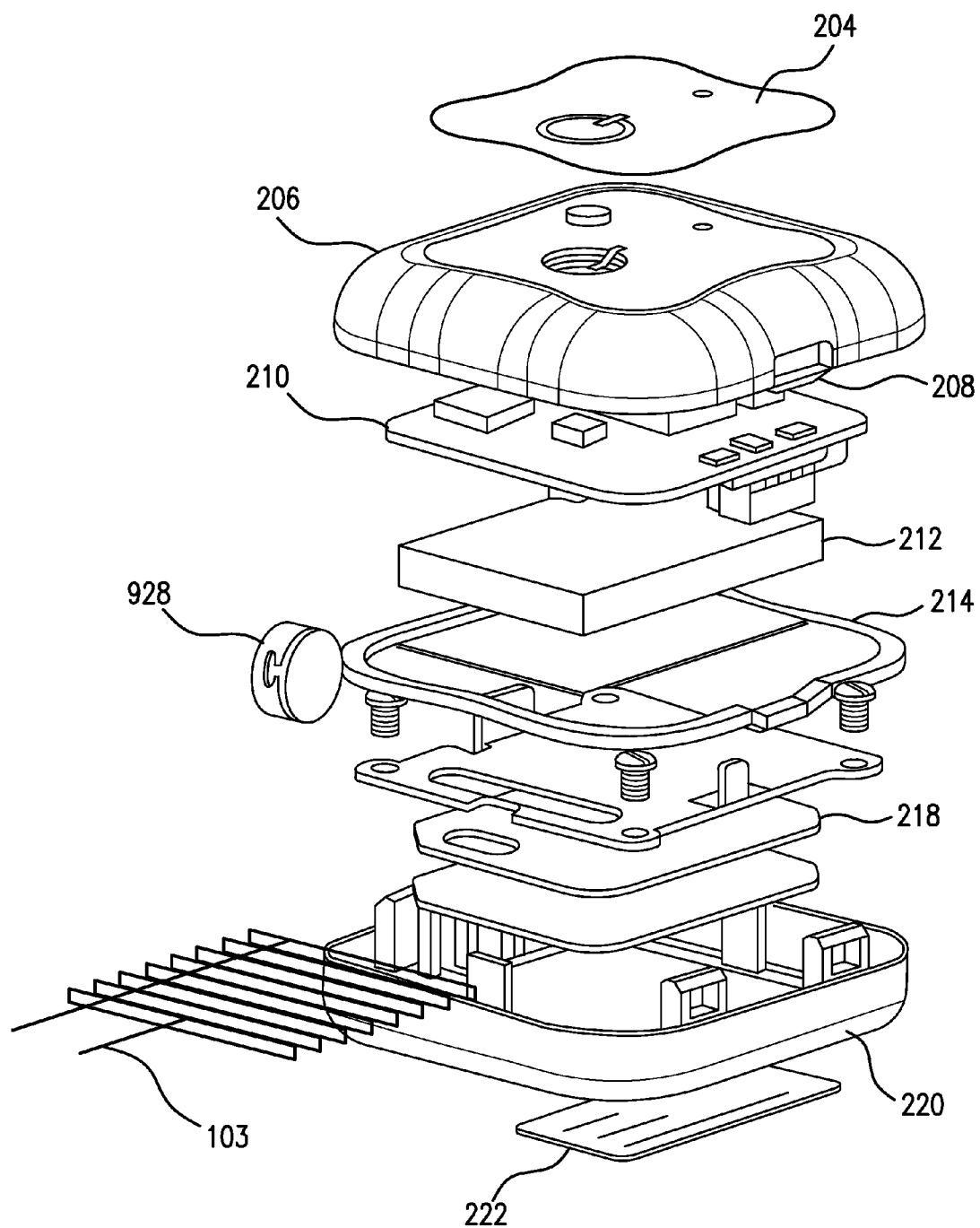
FIG. 9 is an exploded, perspective view of a transceiver embodying aspects of the invention.

FIGS. 8 and 9 are cross-sectional and exploded views, respectively, of a non-limiting embodiment of the transceiver 101, which may be included in the analyte monitoring system illustrated in FIG. 1. As illustrated in FIG. 9, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. However, this is not required, and in some alternative embodiments, the front housing 206 and back housing 220 in another manner (e.g., ultrasonic welding). In some embodiments, the full assembly process may be performed at a single external electronics manufacturer. However, this is not required, and, in alternative embodiments, the transceiver 101 may be performed at one or more electronics manufacturers, which may be internal, external, or a combination thereof. In some embodiments, the assembled transceiver may be programmed and functionally tested. In some embodiments, assembled transceivers 101 may be packaged into their final shipping containers and be ready for sale.

In some embodiments, as illustrated in FIGS. 8 and 9, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, wrist or an upper-arm of a patient body. In some non-limiting embodiments, the transceiver 101 may be suitable for attachment to a patient body by means of a biocompatible patch.

Figure 10A:
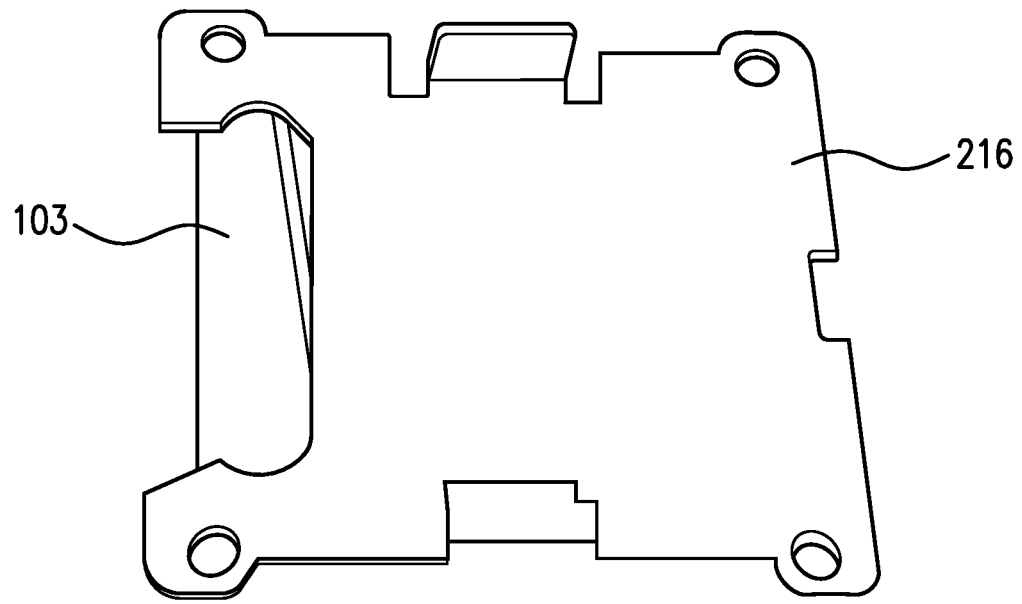
FIGS. 10A and 10B illustrate an inductive element/antenna and reflection plate of a transceiver embodying aspects of the invention.
Figure 10B:
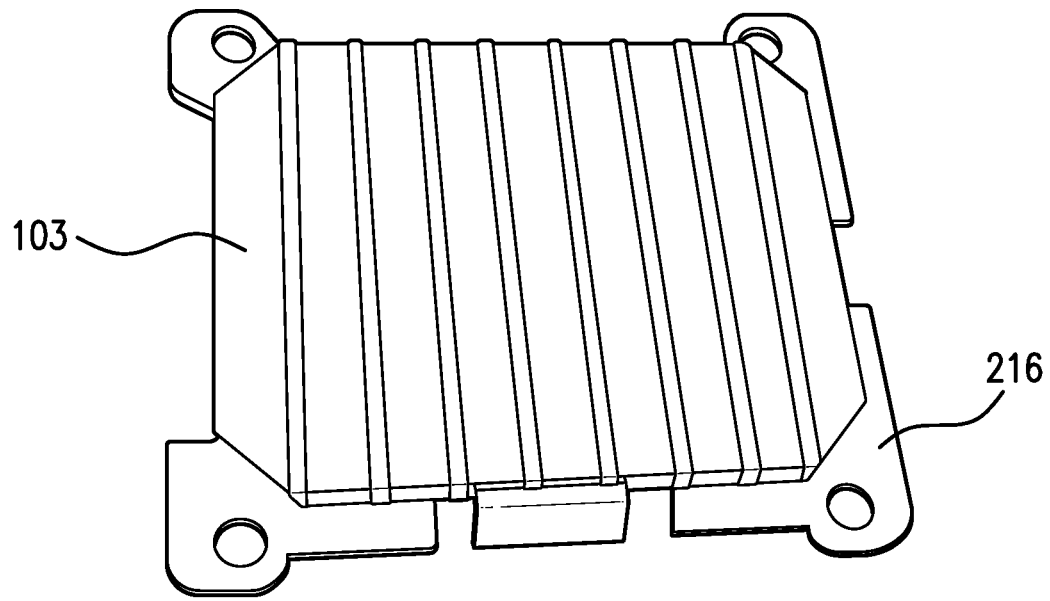

FIGS. 10A and 10B illustrate a non-limiting embodiment of an inductive element 103 and reflection plate 216 of the transceiver 101. In some non-limiting embodiments, the inductive element 103 may be a ferrite antenna. The reflection plate 216 may be made of metal (e.g., aluminum) and may cover all or a portion of the antenna 103. In some embodiments, the reflection plate 216 may have a square, rectangular, triangular, circular, oval, or any other shape suitable for covering all or a portion of the antenna 103. In some embodiments, as illustrated in FIG. 10B, the reflection plate 216 may be shaped to leave a minimum space available for wiring (i.e., connecting the antenna 103 to the PCB assembly 210).

In some embodiments, the reflection plate 216 may be a rigid piece of metal and may have different auxiliary features, such as, for example, holes for mounting the reflection plate 216 to the enclosure and/or PCB assembly 210. However, it is not necessary that the reflection plate 216 have holes, and it is not necessary that the reflection plate 216 be rigid. For example, in alternative embodiments, the reflection plate 216 may be flexible (e.g., kitchen aluminum foil) and may be used with a flexible antenna (e.g., a flexible ferrite antenna). The flexible reflection plate/flexible antenna embodiment may allow the transceiver to more closely conform to the contours of the body. In some embodiments, the antenna 103 may be glued or taped to the reflection plate 216 (e.g., with adhesive or a thin piece of tape/foam).

In some embodiments, the reflection plate 216 may increase the efficiency of the inductive element/antenna 103. For example, in one non-limiting embodiment, the reflection plate 216 may increase the reading range of the transceiver 101 by up to 30% or more. Also, the reflection plate 216 may provide mechanical support. For example, in some non-limiting embodiments, the reflection plate 216 may keep the antenna 103 secure and in place so the antenna 103 does not move inside housing 206 and 220, protect the antenna 103 against mechanical shocks, and/or protect the antenna 103 against random detuning by circuit components of the transceiver (e.g., PCB assembly 210). However, it is not necessary that the reflection plate 216 provide mechanical support, and, in some embodiments where the reflection plate 216 is flexible, the reflection plate 216 may keep antenna in place (i.e., lock it). However, in other alternative embodiments, the reflection plate 216 need not keep antenna 103 in place and clamping (e.g., plastic clamping) may alternatively or additionally be used to keep the antenna 103 in place.

In some embodiments, the antenna system may be a scalable system. That is, the antenna 103 and reflection plate 216 can be smaller or bigger and still retain desired properties and performance.

Figure 11:
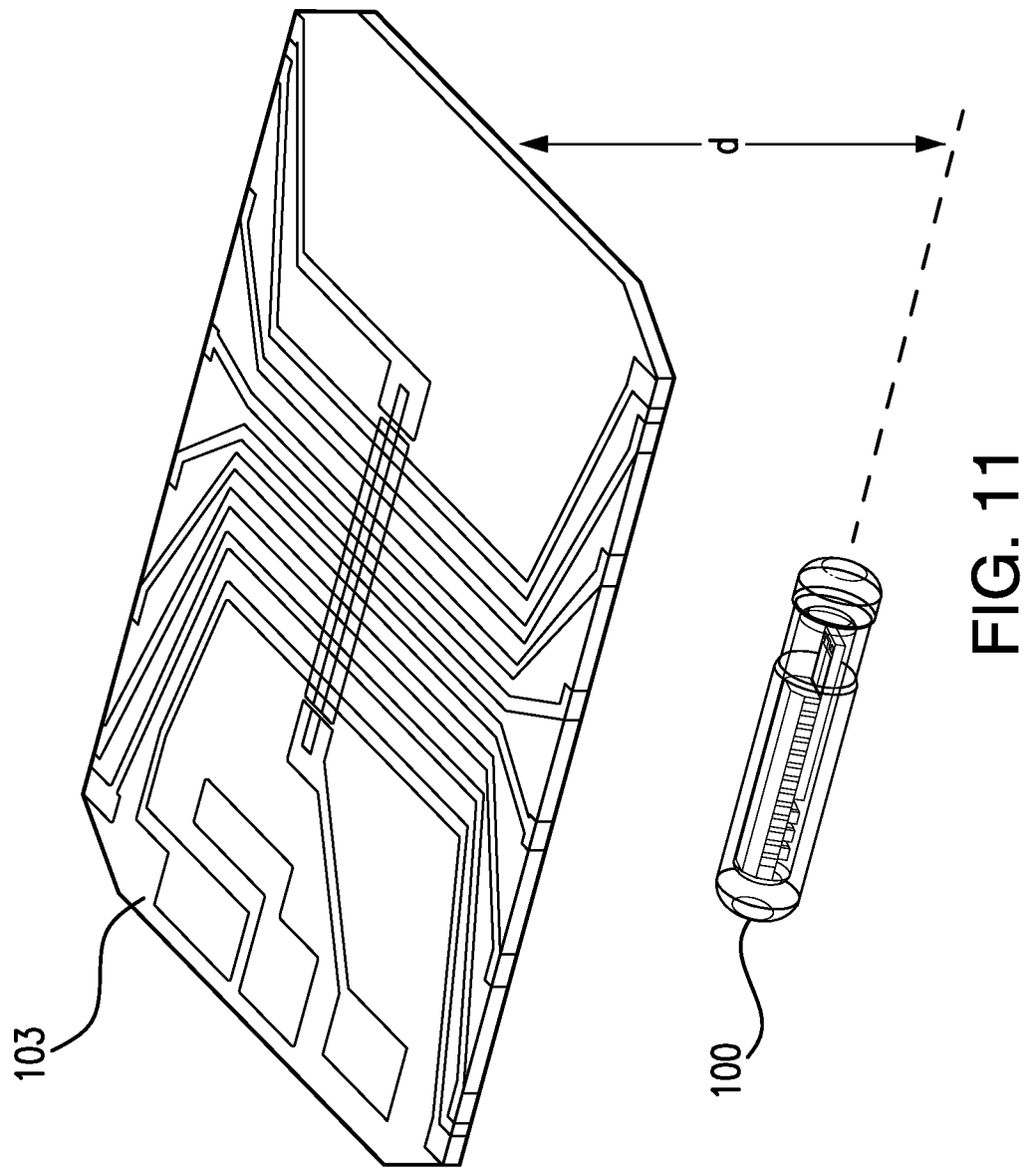
FIG. 11 illustrates a co-planar configuration of a transceiver antenna and implanted sensor in a sensor system embodying aspects of the present invention.

FIG. 11 illustrates a co-planar configuration of a transceiver antenna 103 and an antenna of an implanted sensor 100 in a sensor system embodying aspects of the present invention. The illustrated configuration is co-planar because main axis of the transceiver antenna 103 is parallel to the main axis of the antenna of sensor 100. The illustrated configuration is not coaxial because the transceiver antenna 103 and the antenna of sensor 100 do not share a common axis. In the illustrated configuration, a loosely coupled transformer (e.g., transceiver antenna 103 of transceiver 101) communicates transcutaneously across a distance "d" with an implanted sensor 100. The co-planar inductive link has to transfer power and data transcutaneously to the sensor 100, which may be inserted in the interstitial space. Some embodiments of the present invention may boost the efficiency by using one or more of (a) the reflection plate 216, (b) high quality factor (Q) and high permeability ferrite antennas, (c) a high-efficiency, high power radio frequency (RF) amplifier, and (d) careful antenna design and impedance matching.

Figure 12:
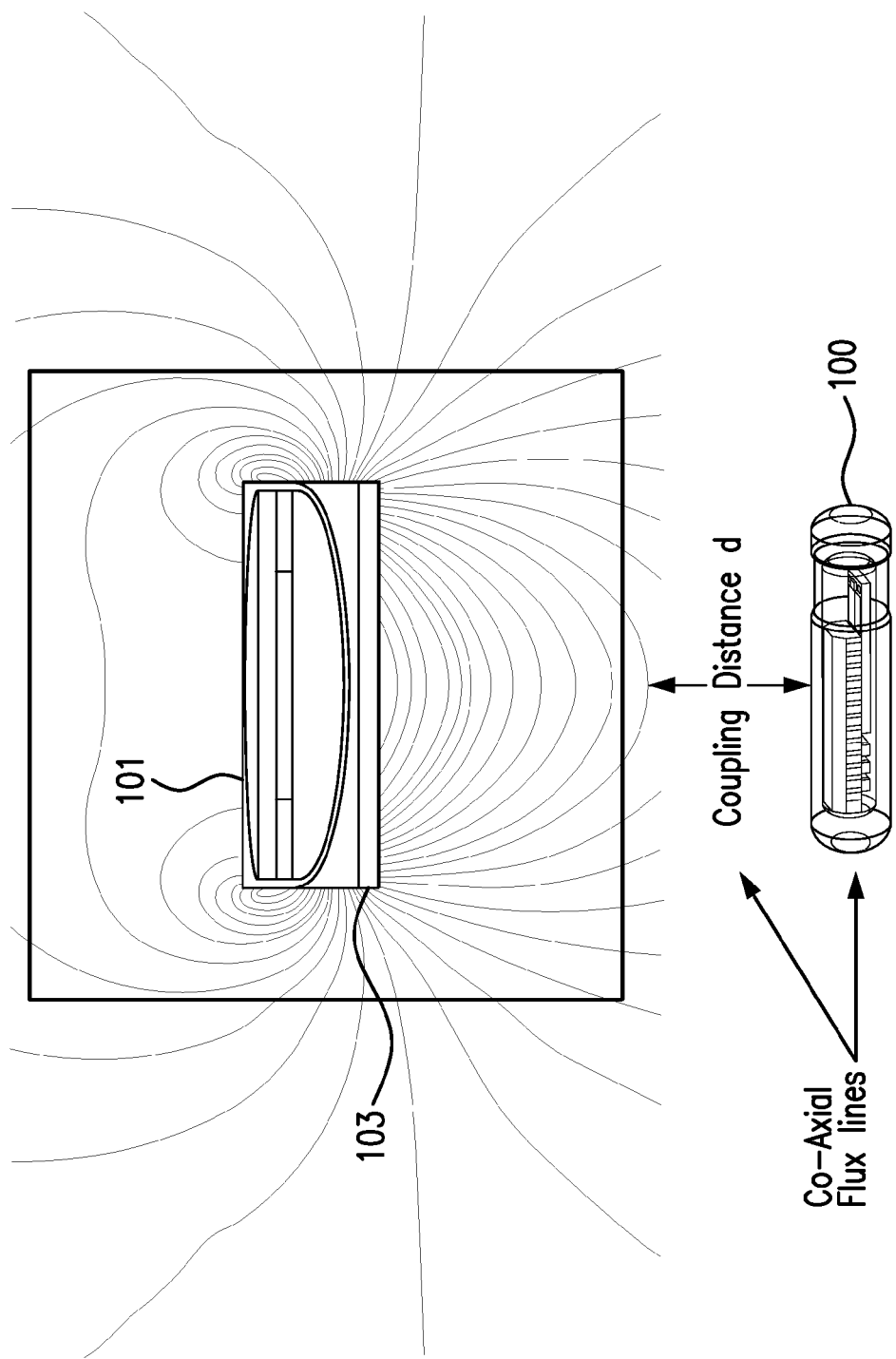
FIG. 12 illustrates magnetic field simulations characterizing flux lines linking a transceiver antenna and a sensor in a sensor system embodying aspects of the present invention.

FIG. 12 illustrates magnetic field simulations characterizing flux lines linking the transceiver antenna 103 and the sensor 100 in a cross-section of the system illustrated in FIG. 11 with an embodiment of the transceiver 101 having a reflection plate 216. In particular, FIG. 12 shows the effect of the reflection plate 216 on the flux lines, which are focused uniformly beneath the transceiver 101. Thus, in some embodiments, the reflection plate 216 may help produce a stronger inductive link between the transceiver antenna 103 and the sensor 100. Moreover, the flux lines created by the transceiver 101 having the reflection plate 216 may allow for flexibility in the alignment of the transceiver antenna 103 and sensor 100 and/or enable a wearable, patient placed telemetry system.

In some embodiments, the sensor 100 may be equipped with highly miniaturized coil antenna 114 on ferrite substrate (e.g., ferrite core 222), and the ferrite substrate may greatly increase both the operational and communication range. The antenna 103 may also be equipped with a ferrite substrate. The ferrite substrates may be high Q and high permeability ferrite substrates. The Q or quality factor is a dimensionless parameter that describes how under-damped an oscillator or resonator is, or equivalently, characterizes a resonator's bandwidth relative to its center frequency. Higher Q indicates a lower rate of energy loss relative to the stored energy of the resonator; the oscillations die out more slowly. Permeability is the degree of magnetization of a material in response to a magnetic field. In some embodiments, the ferrite substrates may help to decrease the overall size of the transceiver antenna 103 and sensor antenna 114 while maintaining or even enhancing their performance. For example, in one non-limiting embodiment, the ferrite substrates may be NiZn based ferrite materials.

Figure 13:
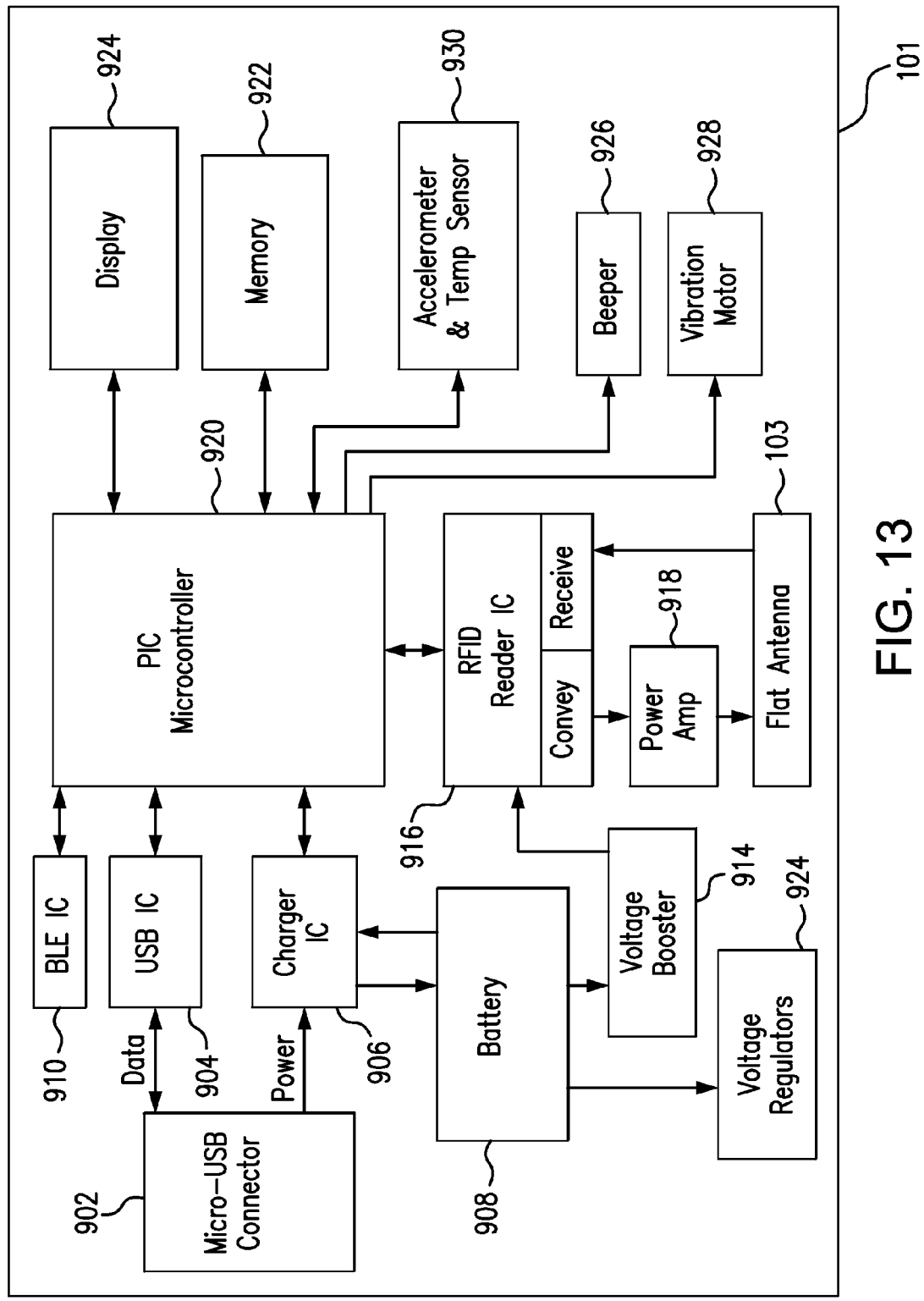
FIG. 13 is a schematic view illustrating a transceiver embodying aspects of the present invention.

FIG. 13 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer or smart phone. The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery).

In some embodiments, the transceiver 101 may have a wireless communication IC 910, which enables wireless communication with an external device, such as, for example, a personal computer or smart phone. In one non-limiting embodiment, the communication IC 910 may employ a standard, such as, for example, a Bluetooth Low Energy (BLE) standard (e.g., BLE 4.0), to wirelessly transmit and receive data to and from an external device.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In the illustrated embodiment, the inductive element 103 is a flat antenna. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data and/or control the RFID reader IC 916 to convey data via the inductive element 103. The PIC microcontroller 920 may also control processing of data received via the inductive element 103, connector 902, or wireless communication IC 910.

In some embodiments, the transceiver 101 may include a display 924 (e.g., liquid crystal display), which PIC microcontroller 920 may control to display data (e.g., glucose concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the PIC microcontroller 920.

Figure 14:
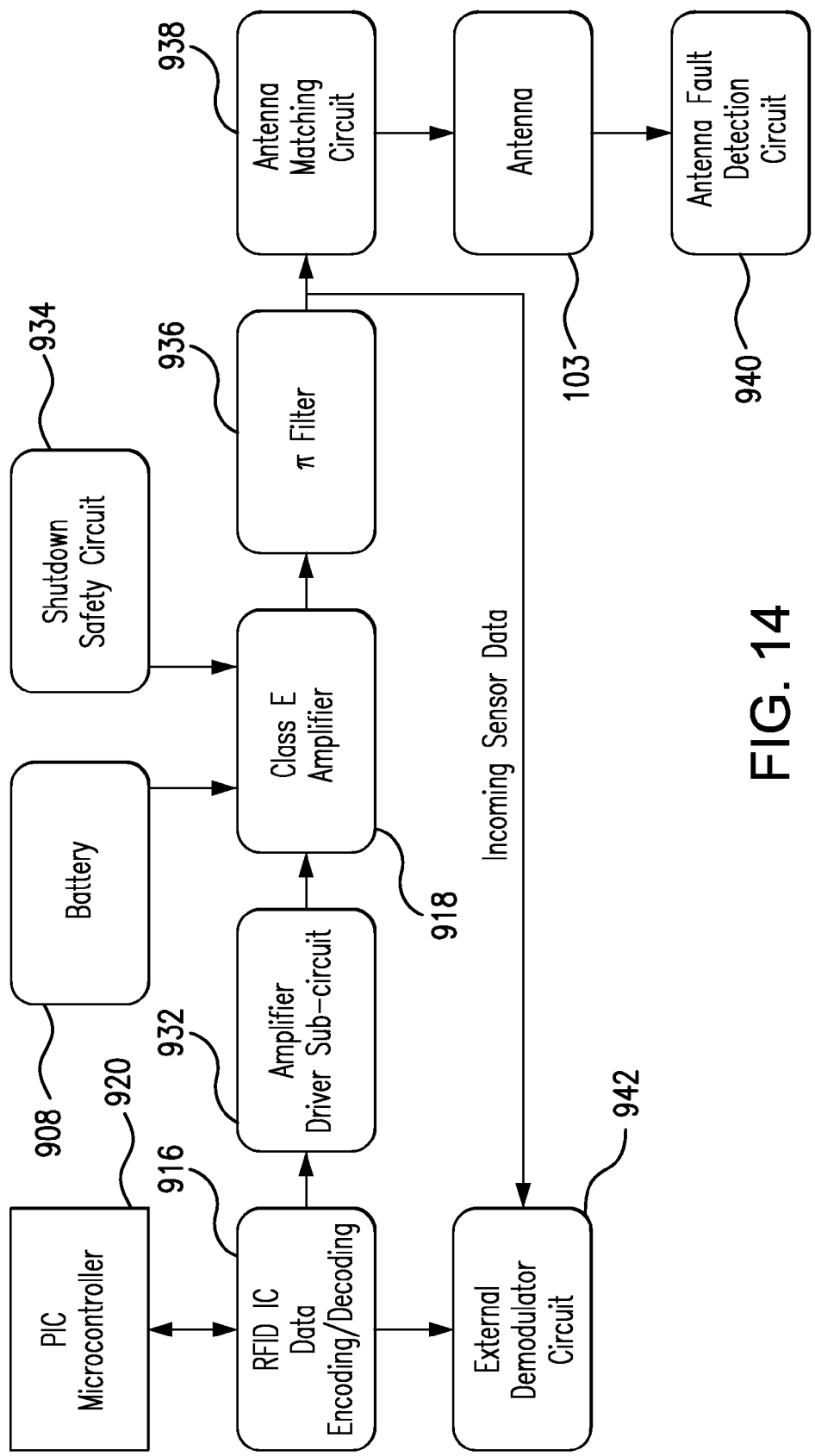
FIG. 14 is a schematic view illustrating a transceiver embodying aspects of the present invention.

In some embodiments, the circuitry of the transceiver 101 may be configured to provide a strong enough magnetic field to provide operating power to the sensor 100 over up to a required range (e.g., 0.5 inches, 0.75 inches, or 1 inch or more). In some embodiments, the amplifier 918 provides the RF power transmitted through transceiver antenna 103 to the sensor antenna 114 in order to provide power to run the sensor 100 and for the sensor 100 to transmit data back to the transceiver 101. In some non-limiting embodiments, as illustrated in FIG. 14, the amplifier 918 of transceiver 101 may be a Class E amplifier, which is a class of switching mode power amplifiers. See, e.g., N. O. Sokal and A. D. Sokal, "Class E—A New Class of High-Efficiency Tuned Single-Ended Switching Power Amplifiers", IEEE Journal of Solid-State Circuits, vol. SC-10, pp. 168-176, June 1975. HVK. A Class E amplifier may be characterized by high efficiency and linear modulation characteristics and suitable for the inductive load applications. In embodiments where the amplifier 918 is a Class E amplifier, the amplifier 918 may provide maximum output power for a given antenna 103 and battery 908 and/or an increase in reading range (e.g., a reading range of up to 1 inch or more). However, the amplifier 918 is not required to be a Class E amplifier, and, in some alternative embodiments, the amplifier 918 may be a different type of amplifier, such as, for example and without limitation, a Class D amplifier or a Class F amplifier.

In some embodiments, the transceiver 101 may include one or more auxiliary sub-circuits. In some non-limiting embodiments, as illustrated in FIG. 14, the auxiliary sub-circuits may include one or more of an amplifier driver sub-circuit 932, shutdown safety circuit 934, a it filter (i.e., pi filter or capacitor-input filter) 936, antenna matching circuit 938, antenna fault detection circuit 940, and external demodulator circuit 942. The amplifier driver sub-circuit 932 may be configured to match an output impedance of the RFID reader IC 916 with the input impedance of the amplifier 918. In one non-limiting embodiment, the amplifier driver sub-circuit 932 may be configured to drive a MOSFET's gate in the amplifier 918 in order to match both MOSFET's gate input impedance and the RFID reader IC 916 output impedance and increase gate driving voltage. The amplifier driver sub-circuit 932 may allow driving the gate with high voltage (e.g., 11 Vpp), which may lead to decreased losses in MOSFET, maximum efficiency of amplifier, and a longer sensor reading range. The shutdown safety circuit 934 may be a hardware "fuse" to shut down the amplifier 918 to prevent excessive heating of the transceiver antenna 103 if the transceiver software gets locked and the field stays on. By preventing excessive heating of the transceiver antenna 103, the shutdown safety circuit 934 prevents possible damage to the transceiver circuitry (e.g., PCB assembly 210), data collection problems, and/or user discomfort that may be caused by excessive heating of the transceiver antenna 103. In some embodiments, the shutdown safety circuit 934 may shut down the amplifier 918 after a predetermined amount of time (e.g., 400 ms). The it filter 936 may filter higher harmonics. The antenna matching circuit 938 may provide good matching between the output impedance of amplifier 918 and the input impedance of antenna 103 and lead to maximized power efficiency. The antenna fault detection circuit 940 may provide an indication of an antenna failure/no power mode. In some embodiments, the antenna fault detection circuit 940 may be a "sniffer" that uses a regular inductor (placed in vicinity of antenna) to detect the antenna field and detect its changes. The demodulator circuit 942 may demodulate data received from the sensor 100.

The antenna fault detection circuit 940 may provide an indication when the antenna 103 is not emitting a strong enough RF signal (e.g., because the antenna 103 is broken or there are other hardware issues). In some embodiments, the antenna fault detection circuit 940 does not simply measure the output voltage of the amplifier 918 because the output voltage of the amplifier 918 does not provide sufficient information. In some embodiments, even the power consumption of the amplifier 918 has no straight dependence from the actual power emitted from the antenna 103. For instance, in some non-limiting embodiments, when the amplifier output is open, DC power consumption may be almost the same as with normal working antenna (e.g., 2 W to 3 W, and, when the amplifier output is shorted, consumption is very low (e.g., 0.2 W to 0.3 W). Accordingly, in some embodiments, instead of simply measuring the output voltage or power of the amplifier 918, the antenna fault detection circuit 940 may include an RF receiver (e.g., implemented on the PCB as part of the PCB circuit assembly 210) having a voltage output proportional to the RF field of the transceiver antenna 103.

Figure 15:
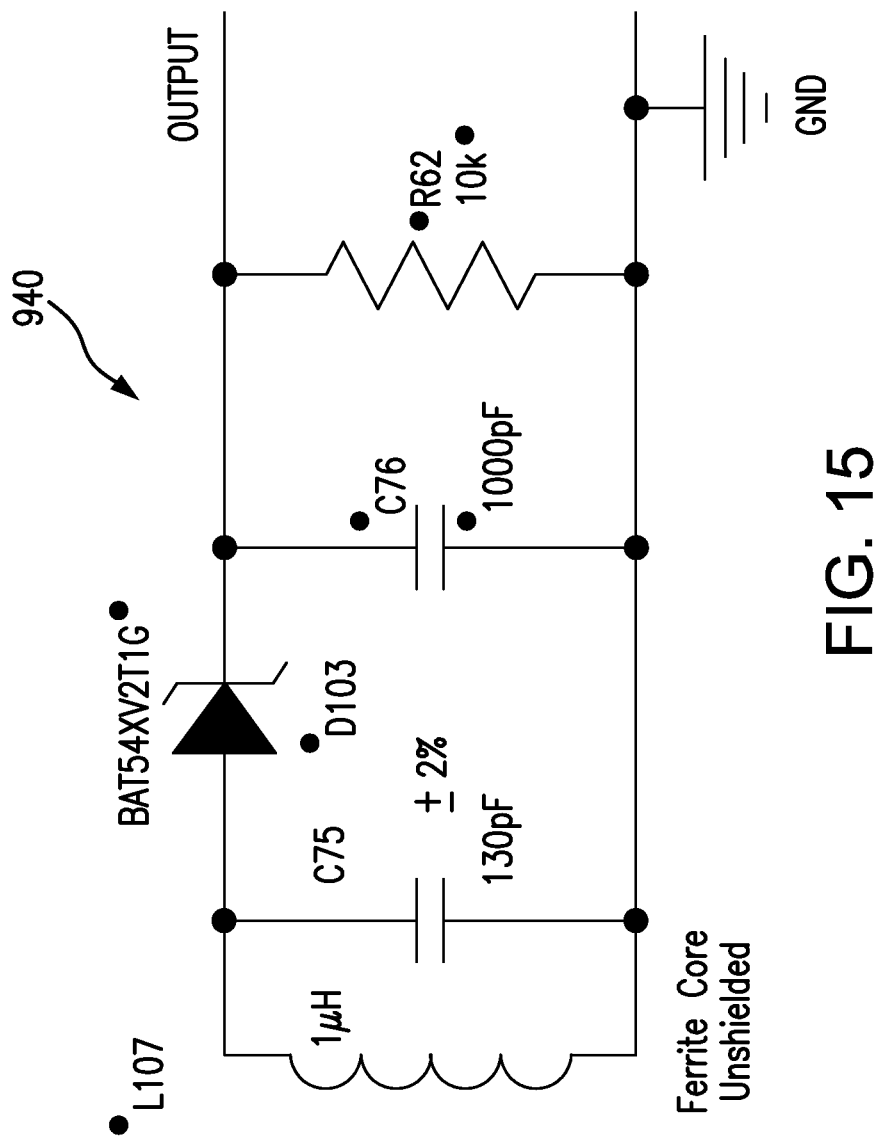
FIG. 15 is a schematic view illustrating an antenna fault detection circuit embodying aspects of the present invention.

FIG. 15 is a schematic view illustrating a non-limiting embodiment of antenna fault detection circuit 940. As illustrated in FIG. 15, the antenna fault detection circuit 940 may include an unshielded inductor L107, which may have, for example, an 0805 size but may also be smaller or bigger). In some embodiments, the unshielded inductor L107 may be a ferrite core inductor. The unshielded inductor L107 may act as small receiving antenna (i.e., a "sniffer"). The direction of the core of inductor L107 may be the same as the direction of the magnetic field of the transceiver antenna 103. In some embodiments, the inductor L107 is not placed at the center of the antenna surface where the received signal is lowest. In preferred embodiments, the inductor L107 may be placed close to the perimeter of the surface of antenna 103.

In some embodiments, the antenna fault detection circuit 940 may include a capacitor C75, a Schottky barrier diode D103, capacitor C76, and resistor R62. The inductor L107 and capacitor C75 with the internal capacity of the Schottky barrier diode D103 may form a resonant circuit at frequency close to 13.56 MHz. However, this is not required, and, in alternative embodiments, the antenna fault detection circuit 940 may include a resonant circuit at a different frequency. In some non-limiting embodiments, for increased resonant frequency accuracy, the inductor L107 may have a 5% tolerance, and the capacitor C75 may have a 2% tolerance. In other embodiments, different tolerances may be used. The capacitor C76 may filter the rectified RF signal, and the resistor R62 may act as a load in order to have the output voltage proportional to the antenna field strength.

In some embodiments, the output from the antenna fault detection circuit 940 may be fed to an analog input (e.g., analog to digital converter (ADC) input) of the microcontroller 920 for voltage measurement (see FIGS. 13 and 14). Based on the voltage measurement, the microcontroller 920 may determine whether the antenna 103 is emitting a strong enough RF signal (e.g., by comparing the measured voltage to a minimum expected voltage). In one non-limiting embodiment, the output from the antenna fault detection circuit 940 may be fed through a standard amplifier/buffer (not shown in FIG. 15) (e.g., with gain K=1) before being fed to the analog input of the microcontroller 920 for voltage measurement. However, the standard amplifier/buffer is not necessary (the input resistance of the microcontroller 920 may be around 10 kOhm, and no significant signal attenuation may occur), and, in some embodiments, the antenna fault detection circuit 940 may not include the standard amplifier/buffer. In some embodiments, the value of resistor R62 could be increased to compensate for an additional load from the ADC pin of the microcontroller 920. For other types of microcontrollers, the design of the antenna fault detection circuit 940 may be further tweaked to obtain optimum results (or amplifier/buffer could be used).

In some embodiments, as illustrated in FIG. 14, the amplifier 918 may feed directly from the battery 908 instead of relying on an intermediate boost converter (e.g., voltage booster 914) or other circuits. In these embodiments, the transceiver 101 may not include a boost converter (e.g., voltage booster 914). By feeding directly from the battery 908, the amplifier 918 may increase the efficiency of the battery 908, which would increase the expected battery life, and may enable the transceiver 101 to be smaller and cheaper as fewer components will be used. In some embodiments, the components of the configuration illustrated in FIG. 14 may be small components decrease the overall size and power requirements of the transceiver 101.

In some non-limiting embodiments, the amplifier 918 (e.g., a Class D, E, or F amplifier) and corresponding matching network illustrated in FIG. 14 may provide sufficient power to the sensor 100 at a required range (e.g., >0.5 inch). In one non-limiting embodiment, the output of the amplifier 918 may be a voltage between 3.4V and 4.2V and a power between 1.1 W and 1.5 W. However, in other non-limiting embodiments, the amplifier 918 may output a different voltage and/or power. In some embodiments, the amplifier 918 may be powered directly from the battery 908 (as illustrated in FIG. 14) in order to increase efficiency and recharge cycle length. In some non-limiting embodiments, back-scattered AM modulation may be used to receive data from the sensor 100. Because its amplitude is very small, the transceiver demodulator circuit 942 may be carefully designed and tuned in order to achieve a high (e.g., >95%) reading success ratio. In some non-limiting embodiments, the transceiver 101 may be capable of operating with sensor distances from skin surface that exceed 0.5 inch, where the signal to noise ratio may drop significantly.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A sensor system for detecting an amount or concentration of an analyte in vivo within a living organism, the sensor system comprising:
   an analyte sensor including a sensor antenna; and
   a transceiver configured to interface with the analyte sensor, the transceiver including a transceiver antenna configured to convey a power signal to the analyte sensor and to receive data signals from the analyte sensor;
   wherein the transceiver antenna and the sensor antenna are configured to provide a co-planar, near field communication telemetry link between the transceiver and the analyte sensor capable of transcutaneous communication;
   wherein the main axis of the transceiver antenna and the main axis of the sensor antenna are not coaxial while providing the telemetry link.

2. The sensor system of claim 1, wherein the sensor antenna includes a ferrite core, and the transceiver antenna includes a ferrite core.

3. The sensor system of claim 2, wherein the ferrite cores have a high quality factor and a high permeability.

4. The sensor system of claim 2, wherein the ferrite cores are an NiZn based ferrite material.

5. The sensor system of claim 1, wherein the transceiver antenna is a flat antenna.

6. The sensor system of claim 1, wherein the transceiver further comprises:
   a battery configured to provide battery power;
   an amplifier configured to amplify the battery power and provide radio frequency (RF) power to the transceiver antenna.

7. The sensor system of claim 6, wherein the provided RF power is sufficient to power the analyte sensor at the distance greater than or equal to 0.5 inches.

8. The sensor system of claim 1, wherein the transceiver antenna and sensor antenna are configured to provide a co-planar, near field communication telemetry link between the transceiver and the sensor capable of transcutaneous communication across a distance greater than or equal to 0.5 inches.

9. The sensor system of claim 1, wherein the analyte sensor is configured to be implanted within the living organism.

10. The sensor system of claim 1, wherein the transceiver is a handheld transceiver.

11. The sensor system of claim 10, wherein the handheld transceiver is a smartphone or tablet.

12. The sensor system of claim 1, wherein the analyte sensor and transceiver are configured such that, while the analyte sensor is implanted beneath the skin of a living animal and the transceiver antenna and the sensor antenna are providing a co-planar, near field communication telemetry link between the transceiver and the analyte sensor capable of transcutaneous communication, a main axis of the transceiver antenna and a main axis of the sensor antenna are parallel to the surface of the skin under which the analyte sensor is implanted.

13. A sensor system for detecting an amount or concentration of an analyte in vivo within a living organism, the sensor system comprising:
   an analyte sensor including a sensor antenna; and
   a transceiver configured to interface with the analyte sensor, the transceiver including a transceiver antenna configured to convey a power signal to the analyte sensor and to receive data signals from the analyte sensor;
   wherein the transceiver antenna and the sensor antenna are configured to provide a co-planar, near field communication telemetry link between the transceiver and the analyte sensor capable of transcutaneous communication;
   wherein the transceiver antenna is a flat antenna;
   wherein the transceiver antenna does not generate a magnetic field coaxially to a main axis of the sensor antenna while providing the telemetry link.

14. A sensor system for detecting an amount or concentration of an analyte in vivo within a living organism, the sensor system comprising:
   an analyte sensor including a sensor antenna;
   a transceiver configured to interface with the analyte sensor, the transceiver including:
      a transceiver antenna configured to convey a power signal to the analyte sensor and to receive data signals from the analyte sensor; and
      a reflection plate configured to focus flux lines linking the transceiver and the analyte sensor uniformly beneath the transceiver;
   wherein the transceiver antenna and the sensor antenna are configured to provide a co-planar, near field communication telemetry link between the transceiver and the analyte sensor capable of transcutaneous communication.

15. A sensor system for detecting an amount or concentration of an analyte in vivo within a living organism, the sensor system comprising:
   an analyte sensor including a sensor antenna; and
   a transceiver configured to interface with the analyte sensor, the transceiver including a transceiver antenna configured to convey a power signal to the analyte sensor and to receive data signals from the analyte sensor;
   wherein the transceiver antenna and the sensor antenna are configured to provide a co-planar, near field communication telemetry link between the transceiver and the analyte sensor capable of transcutaneous communication;
   wherein the main axis of the transceiver antenna does not pass through the circumference of the sensor antenna, and the main axis of the sensor antenna does not pass through the circumference of the transceiver antenna while providing the telemetry link.

* * * * *